US012805946B2

(12) United States Patent
Liu et al.

(10) Patent No.: US 12,805,946 B2
(45) Date of Patent: Nov. 24, 2026

(54) METHOD, EQUIPMENT AND STORAGE MEDIUM FOR NAVIGATING A TUBULAR COMPONENT IN A MULTIFURCATED CHANNEL

(71) Applicant: Precision Robotics (Hong Kong) Limited, Shatin (HK)

(72) Inventors: Ning Liu, Shatin (HK); Ping Lai Benny Lo, Shatin (HK); Hing Kui Wong, Shatin (HK)

(73) Assignee: Precision Robotics (Hong Kong) Limited, Shatin (HK)

( * ) Notice: Subject to any disclaimer, the term of this patent is extended or adjusted under 35 U.S.C. 154(b) by 48 days.

(21) Appl. No.: 18/289,656

(22) PCT Filed: Mar. 29, 2022

(86) PCT No.: PCT/CN2022/083695
§ 371 (c)(1),
(2) Date: Nov. 6, 2023

(87) PCT Pub. No.: WO2022/233201
PCT Pub. Date: Nov. 10, 2022

(65) Prior Publication Data
US 2024/0252260 A1 Aug. 1, 2024

(30) Foreign Application Priority Data
May 6, 2021 (HK) ........................... 22021030451.9

(51) Int. Cl.
*A61B 34/30* (2016.01)
*A61B 1/00* (2006.01)
*A61B 34/10* (2016.01)

(52) U.S. Cl.
CPC ........ *A61B 34/30* (2016.02); *A61B 1/000094* (2022.02); *A61B 34/10* (2016.02);
(Continued)

(58) Field of Classification Search
CPC ... A61B 34/30; A61B 34/10; A61B 1/000094; A61B 2034/105; A61B 2034/107; A61B 2034/301
See application file for complete search history.

(56) References Cited

U.S. PATENT DOCUMENTS 10,238,455 B2 * 3/2019 Krimsky ................ G16H 50/50
11,188,285 B2 * 11/2021 Kehat .................. A61B 1/2676
(Continued)

FOREIGN PATENT DOCUMENTS

CN 103648361 A 3/2014
CN 104050348 A 9/2014
(Continued)

OTHER PUBLICATIONS

International Search Report from PCT International Application No. PCT/CN2022/083695 dated Jun. 27, 2022.
(Continued)

*Primary Examiner* — Jason Holloway
(74) *Attorney, Agent, or Firm* — Budzyn IP Law, LLC

(57) ABSTRACT

A method, equipment and storage medium for navigating a tubular component in a multifurcated channel. The method includes the steps of: acquiring a three-dimensional model of the multifurcated channel; planning navigation information for the tubular component within the multifurcated channel according to the three-dimensional model; and driving the tubular component to move according to the navigation information, in response to the input of a forward/backward signal. The equipment includes a scanner configured to acquire the three-dimensional model of the multifurcated channel; a planning device configured to plan the navigation information for the tubular component within the multifurcated channel according to the three-dimensional model; and a tubular component feeding device configured to drive the tubular component to move accord-
(Continued)

ing to the navigation information, in response to the input of the forward/backward signal. The equipment can reduce the difficulty of operation and provide better safety and reliability in operation.

6 Claims, 7 Drawing Sheets

(52) U.S. Cl.
CPC ... *A61B 2034/105* (2016.02); *A61B 2034/107* (2016.02); *A61B 2034/301* (2016.02)

(56) References Cited

U.S. PATENT DOCUMENTS

| | | | | |
|---|---|---|---|---|
| 2010/0310146 | A1* | 12/2010 | Higgins | G06T 7/162 345/419 |
| 2012/0289777 | A1 | 11/2012 | Chopra et al. | |
| 2014/0281961 | A1* | 9/2014 | Baker | G06F 3/0484 715/705 |
| 2015/0216398 | A1* | 8/2015 | Yang | G01J 3/0208 600/109 |
| 2017/0084027 | A1* | 3/2017 | Mintz | A61B 1/00194 |
| 2019/0228528 | A1* | 7/2019 | Mintz | A61B 1/000094 |
| 2019/0314005 | A1* | 10/2019 | Ishihara | A61B 34/74 |
| 2019/0343581 | A1* | 11/2019 | Panescu | A61B 34/20 |
| 2019/0365486 | A1* | 12/2019 | Srinivasan | A61B 34/20 |
| 2020/0078103 | A1* | 3/2020 | Duindam | A61B 1/009 |
| 2020/0275982 | A1 | 9/2020 | Thienphrapa et al. | |
| 2023/0404689 | A1* | 12/2023 | Truckai | A61B 34/30 |

FOREIGN PATENT DOCUMENTS

| | | | |
|---|---|---|---|
| CN | 105231978 | A | 1/2016 |
| CN | 110831481 | A | 2/2020 |
| CN | 111479507 | A | 7/2020 |
| CN | 112089392 | A | 12/2020 |

OTHER PUBLICATIONS

Written Opinion from International Application No. PCT/CN2022/083695 dated Jun. 29, 2022.
Office Action from Hong Kong Application No. 22021030451.9 dated Aug. 21, 2023.

* cited by examiner

METHOD, EQUIPMENT AND STORAGE MEDIUM FOR NAVIGATING A TUBULAR COMPONENT IN A MULTIFURCATED CHANNEL

CROSS-REFERENCE TO RELATED APPLICATIONS

This Application is a National Stage Application under 35 U.S.C. § 371 of PCT Application No. PCT/CN2022/083695, filed Mar. 29, 2022 which claims priority to Hong Kong Patent Application No. 22021030451.9, filed May 6, 2021, the entire contents of which are incorporated by reference herein.

TECHNICAL FIELD

The present application relates to the technical field of navigation within a pipe, and more particular to a method, equipment and storage medium for navigating a tubular component in a multifurcated channel.

BACKGROUND OF THE INVENTION

Pipe inspection usually requires insertion of a flexible tubular component with embedded camera at the tip. Regarding similar medical applications like endoscopy; flexible thin endoscopes are inserted into patient bodies through natural orifices (mouth, nose, anus etc.) to examine the internal situations or perform treatment. Navigation of endoscopes is critical for the success of interventions, but it is also a challenging task, especially for bronchoscopy.

Human respiratory tree has a complex branching structure with more than 20 generations. In order to steer the bronchoscope to target positions, physicians have to carefully observed image feedbacks from the camera, rely on their knowledge of anatomy and memory of preoperative CT scans to mentally track the scope locations. It becomes more and more difficult as the bronchoscope approaches peripheral areas. Besides, physicians have to operate the bronchoscope with at least three degrees of freedom. This not only increases the mental burden of operators but also raises high requirements for their operation techniques. Even experienced physicians could probably make mistakes and have to try multiple times to enter the correct airway branch, prolonging the intervention and lowering the yield. Moreover, due to the burden of navigation, physicians may not pay enough attention to bronchoscopic images along the path and miss diseased tissues.

With the development of artificial intelligence and surgical robotics, automatic navigation technology is promising to solve the above issues. This patent proposes a semi-automatic navigation framework that the operator only needs to control the forward and backward movement of the scope, the surgical robot can localize the scope and automatically adjust the scope orientations according to predefined or temporarily decided paths. Compared with fully automatic navigation, the proposed technology has the following advantages. Firstly, the physicians can stop at any time, thus is safer when the navigation algorithm goes wrong. Secondly, it allows seamless manual interruptions to further examine interested tissues along the path, or change the path to new targets.

SUMMARY OF THE INVENTION

In order to solve or at least partly solve the aforementioned technical problems, the present application proposes a method, equipment and storage medium for navigating tubular component in a multifurcated channel.

The navigation method comprises the steps of: acquiring a three-dimensional model of a multifurcated channel; planning navigation information for the tubular component within the multifurcated channel according to the three-dimensional model; driving the tubular component to move according to the navigation information, in response to the input of a forward/backward signal.

The navigation equipment comprises: a scanner configured to acquire a three-dimensional model of a multifurcated channel; a planning device configured to plan navigation information for the tubular component within the multifurcated channel according to the three-dimensional model; a tubular component feeding device configured to drive the tubular component to move according to the navigation information in response to the input of a forward/backward signal.

The computer-readable storage medium has stored a computer program, which is able to perform the respective steps of the aforementioned method, when executed by a processor.

Compared with prior art, the technical solution of the present application can greatly reduce the difficulty of operation, so physicians can focus on more important actions, and better safety and reliability can be expected in operation.

BRIEF DESCRIPTION OF THE DRAWINGS

To better explain embodiments of the present application, relevant drawings will be briefly described below. It is to be understood that, drawings described below are only used to illustrate certain embodiments of the application, and those of ordinary skill in the art can perceive many other technical features and connections that are not mentioned herein, based on these drawings.

REFERENCE SIGNS

Figure 1:
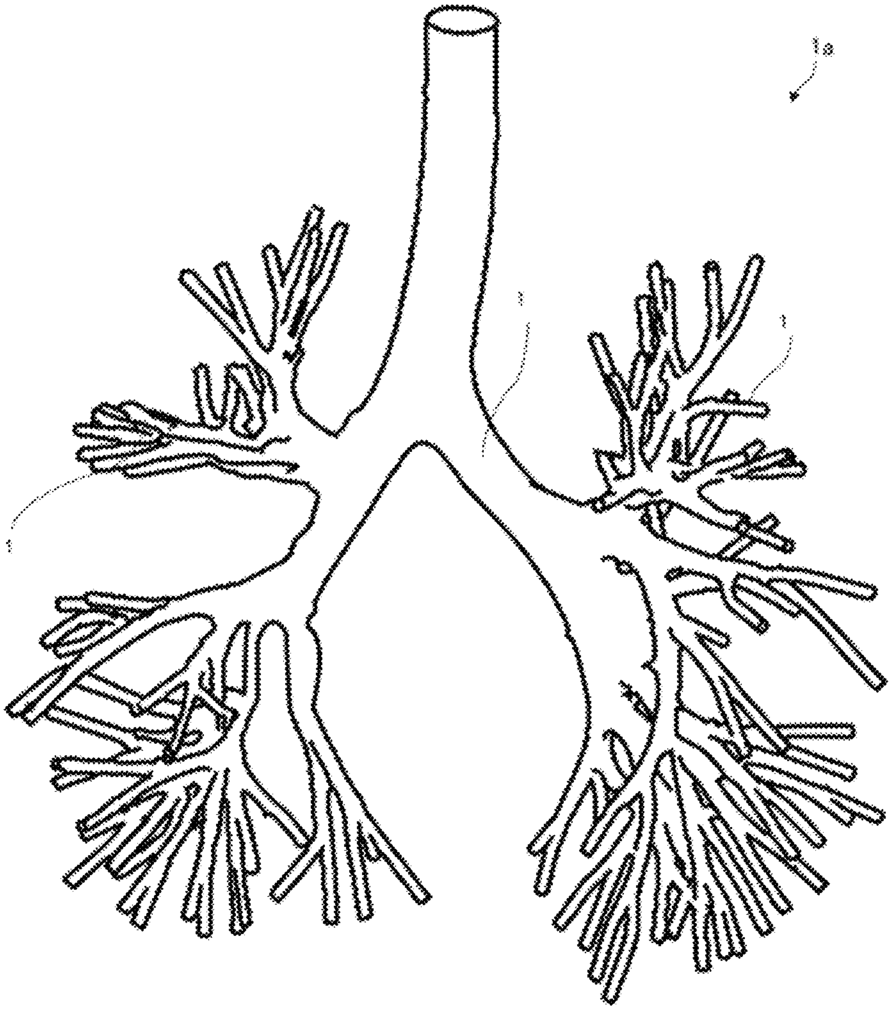
FIG. 1 is a schematic structural view of a multifurcated channel.

1: multifurcated channel; 1*a*: three-dimensional model; 1*b*: target channel; 2: tubular component; 2*a*: head; 3: navigation path; 3*a*: first position; 3*b*: second position; 3*c*:

third position; 4*a*: first visual field; 4*b*: second visual field; 4*c*: third visual field; 5: navigation equipment for a tubular component in the multifurcated channel; 51: scanner; 52: planning device; 53: tubular component feeding device; 53*a*: localizing device; 53*b*: correcting device; 53*c*: visual field acquisition device; 54: resistance feedback device; 55: tactile feedback device.

DETAILED DESCRIPTION OF EMBODIMENTS

The present application will be described in detail below in conjunction with drawings.

Referring to FIGS. 1-10, the present application proposes a method for navigating a tubular component in a multifurcated channel, comprising the steps of: acquiring a three-dimensional model 1*a* of a multifurcated channel 1; planning navigation information for a tubular component 2 within the multifurcated channel 1 according to the three-dimensional model 1*a*; driving the tubular component 2 to move according to the navigation information, in response to the input of a forward/backward signal.

Correspondingly, the present application further proposes an equipment 5 for navigating a tubular component in a multifurcated channel, comprising: a scanner 51 configured to acquire a three-dimensional model 1*a* of the multifurcated channel 1; a planning device 52 configured to plan navigation information for the tubular component 2 within the multifurcated channel 1, according to the three-dimensional model 1*a*; a tubular component feeding device 53 configured to drive the tubular component 2 to move according to the navigation information, in response to the input of a forward/backward signal.

The tubular component 2 may be a rigid pipe or a flexible hose. The channel that the tubular component 2 enters may be a channel in the medical or non-medical field. In the medical field, the multifurcated channel 1 may be a channel of digestive tract, vessel, breathing passages, etc. of the human body. However, the present application is not limited to such specific application scenarios of the multifurcated channel 1. Human airways, due to their complex structures, will be mainly described herein, as an illustrative example shown in FIG. 1. In an embodiment, construction of the three-dimensional model 1*a* of the multifurcated channel 1 can be realized by a scanning technology, such as CT and MRI, in conjunction with medical image segmentation technology.

Additionally, the multifurcated channel 1 in the medical field can be a model of human respiratory tree, which is applicable to medical training, teaching and even examinations, for example. Operating the tubular component 2 in the model of human airways for examination or treatment can help physicians accumulate experience and transit from medical training to clinical surgery. For experienced physicians, the present application can also be applied to scoring assessment, working competition, etc.

Figure 2:
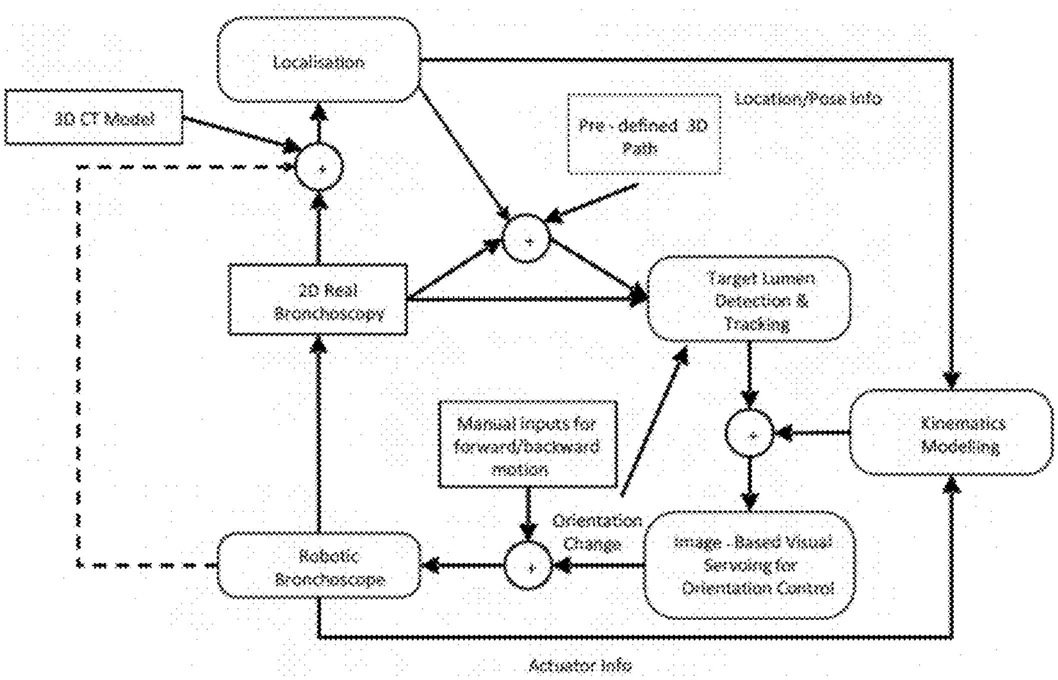
FIG. 2 is a flowchart of a method for navigating a tubular component in the multifurcated channel.
Figure 3:
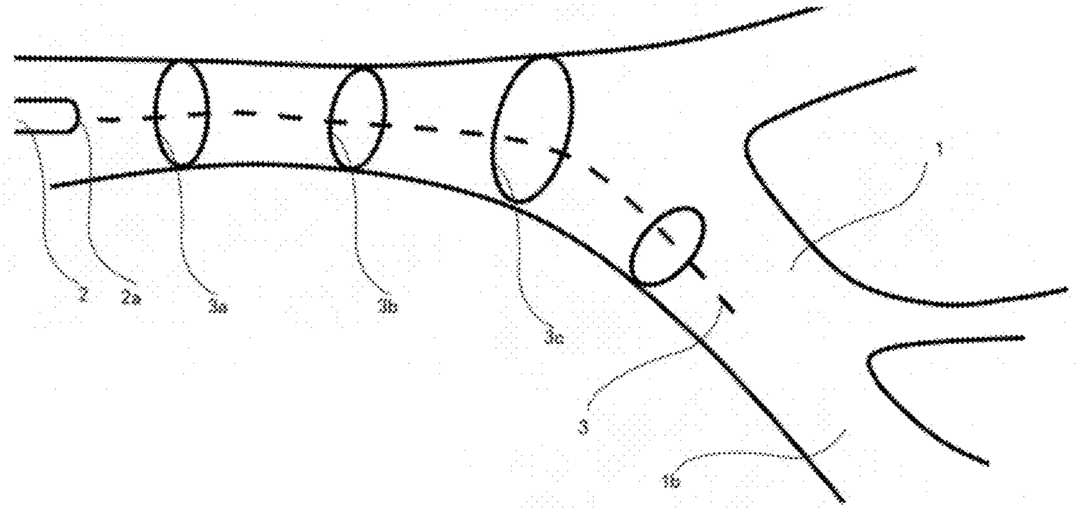
FIG. 3 is a schematic view of acquiring the visual field in front of a head of the tubular component.
Figure 4:
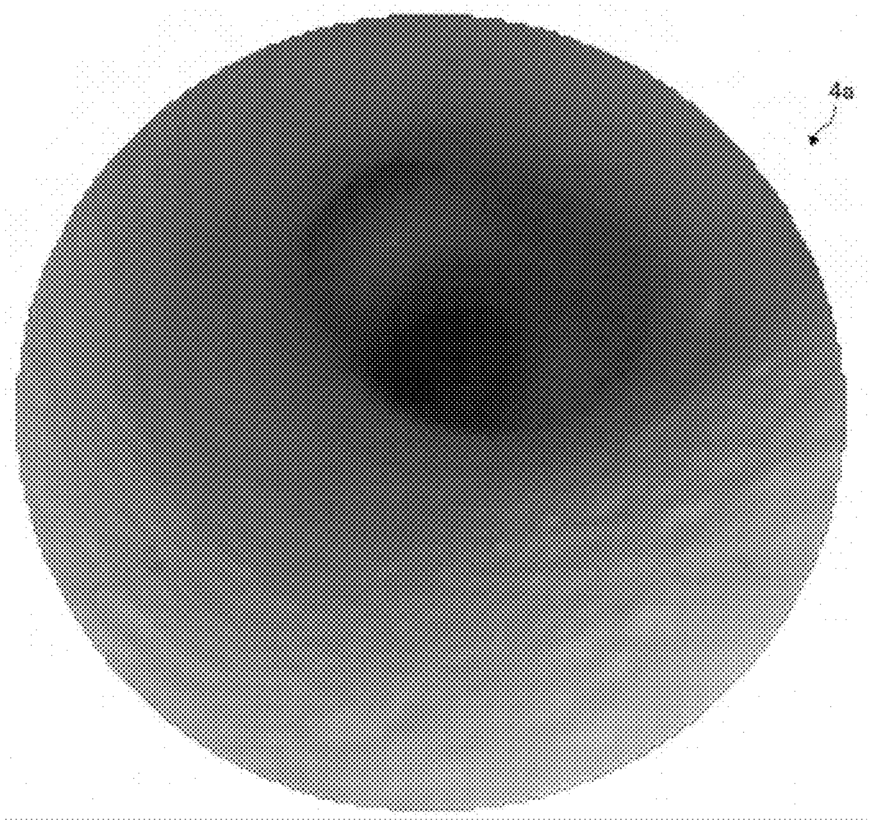
FIG. 4 is a schematic view of a shot photograph of the head of the tubular component in a first visual field at a first position.

As shown in FIG. 2, an embodiment of the present application uses the three-dimensional model 1*a* established by scanning results to plan navigation information, automatically controls the head 2*a* orientation of the tubular component 2 through a computer, and manually controls the advance and retreat of the tubular component 2 by a physician.

The navigation information may include the path planning information, pose information, current location information, and other information applied to assist the tubular component in a semi-automatic movement. Among them, the path planning information can be obtained through planning in advance or real-time based on the current position and the target position; the pose information can be obtained through detection by sensor, or calculated from the rotation numbers of motor in combination with a kinematic model; the location information can be calculated by a localizing module based on various information like endoscopic images. The pose information may further include the translational speed, rotation speed, etc. of the tubular component 2 while the motion of its head end is adjusted at a certain position. In order to better acquire the pose information and location information, a plurality of different sensors may be arranged around the tubular component 2, and distributed at various positions to offer motion feedback. For example, an optical sensor may be used to measure the translational/rotation speed or the travel distance of the tubular component 2 in a non-contact manner, so as to obtain abundant pose information without affecting the motion of tubular component 2.

Specifically, the navigation information may further include: a navigation path 3 to reach the target position along the multifurcated channel 1; orientation parameters of the head 2*a* of the tubular component 2 at various positions, while it travels along the navigation path 3.

Based on the accurate bronchoscope localization and the advanced control algorithms, the robotic system of the present application can decide optimal bending angles and rotation angles of the tubular component 2, so as to optimally drive it from a start point to the target position. For example, in a straight channel, each orientation parameter of the tubular component 2 is ( ) respective orientation parameters are set in a bifurcated channel, and thus the bending angles and rotation angles of the tubular component 2 ought to be changed.

In view of the above and further referring to FIG. 2 wherein the use of endoscope is taken as an example, an embodiment of the present application proposes a practical application process of the semi-automatic navigation method for a tubular component:

(1) The robotic bronchoscope is inserted into the patient's body according to the pre-defined 3D path in the planed path information. The bronchoscope continuously acquires real endoscopic images of internal cavities of the patient. Here, 2D or stereo images may be obtained in this case depending on the type of endoscope.

(2) With the aid of the acquired real endoscopic images, the localization of its own position may be performed. Meanwhile, pose information and current location information are provided for kinematics modeling of the tubular component.

(3) In the course of advancing the bronchoscope, target lumen detection and tracking may be conducted in conjunction with the pre-defined 3D path, the pose information and current location information.

(4) The bronchoscope may perform image-based visual servoing for orientation control, on the basis of the feedback from the above real endoscopic images, and the path and orientation change are continuously conducted.

(5) In the whole process, physician only needs to manually input the forward and backward motion instructions, and no other operations are further required.

More specifically, in step (1), physicians may determine the location of a specific interested area in the three-dimensional model 1*a* according to the scanning results, i.e., the target position. With the start point (e.g. airway is usually the start point for bronchoscopy) and target position, it is able to plan navigation information in the three-dimensional model 1*a*. The tubular component 2 may naturally move with multiple degrees of freedom according to navigation information.

In actual operation, physicians only need to decide whether to advance or retract the tubular component 2 with a simple button or pedal. Of course, physicians can also interrupt the current navigation task at any time and turn to the manual operation, or manually change the navigation path 3.

Generally, the present application proposes a semi-automatic navigation method for tubular components. Physicians only need to control one degree of freedom (forward/backward), while the other degrees of freedom can be autonomously controlled by the robotic system according to the navigation information, to realize navigation of the tubular component. Compared with prior art, since the movement route of the tubular component 2 is preset in the navigation information, the head 2*a* orientation of the tubular component 2 can be automatically adjusted according to the navigation information. Given that the navigation path 3 has been confirmed, physicians only need to manipulate the tubular component 2 so that it moves forward or backward, or stops in the confirmed navigation path 3, to fulfil the medical purpose. In operation, physicians do not need to spend extra mental burden on adjusting the orientation or angles of the tubular component 2, but can focus more on medical operations, such as checking lesions or performing surgery. Thus, the present application can greatly reduce the difficulty of operation, as well as the physical and mental burden of physicians. Additionally, physicians can pause or change objects at any time during the operation, which is significantly convenient.

In particular, when the CT scan result of the patient shows multiple lesion points, multiple target points can be marked in the three-dimensional model 1*a*. In this case, the navigation path 3 planned may have multiple target points. For example, where multiple target points are located in different branches, physicians can operate the tubular component 2 according to the navigation path 3 during preoperative inspection, to return it to a main path after completing the inspection of a first lesion point in a first branch, and then make it enter a second branch to check a second lesion point. Compared with a solution where physicians directly navigate the tubular component 2 to the second lesion point according to experience, the present application can improve the accuracy of actual operation with the aid of the navigation path 3, and prevent getting lost in the multifurcated channel 1. In minimally invasive surgery, physicians can also set a new target point in operation at any time, such as continuing to go deep after eliminating the first lesion point in the first branch, to improve surgery efficiency. Of course, physicians may mark a special location and change the navigation path 3 to get around certain anatomical structures.

Unlike traditional robots like a robotic arm with rigid links, the pose and location of a flexible endoscope cannot be fully controlled by the actuation device. In fact, a flexible endoscope is under-actuated. It only has 3 degrees of freedom (DoFs), while 6 DoFs are required to move in a 3D space. It relies on the contact with human anatomy (e.g. airway walls) to adjust its own pose. However, the anatomical cavities are larger than the scope and even moving and deformable in bronchoscopy. As a result, the endoscope could easily deviate from the pre-defined path and has to steer itself accordingly. To this end, the present navigation method further comprises the steps of: determining position of the tubular component 2 in the multifurcated channel 1; correcting current orientation of the head 2*a* of the tubular component 2 in combination with the localization information, according to the determined position.

Correspondingly, the tubular component feeding device of the present application may further include a localizing device 53*a* and a correcting device 53*b*. The localizing device 53*a* is configured to determine position of the tubular component 2 in the multifurcated channel 1, and also to identify channels in the visual field based on the acquired visual field in front of the head of the tubular component 2. The correcting device 53*b* is used to correct current head orientation of the tubular component 2 in combination with the navigation information, according to the determined position.

The accuracy and reliability of operation can be improved by determining position of the tubular component 2 in the multifurcated channel 1. Different localization algorithms may apply different intraoperative information, besides the preoperative 3D model. For example, some algorithms may only rely on the real-time intraoperative 2D image of the endoscope to match the virtual bronchoscopy rendered by the preoperative 3D model, for localization. However such algorithms may not be robust, therefore other kinds of information could be introduced, such as: (1) the kinematics information of the endoscope, including the depth of the endoscope and the rotation angles, which can be measured by an optical sensor, or calculated by an endoscope robot based on the rotation status of the motor and its own kinematics model; (2) an electromagnetic sensor for three-dimensional localization integrated into the endoscope head. In brief, the influence of airway motion and deformation caused by breath on the localization algorithm can be removed by a combination of sensed information in multi-dimension, leading to more robust localization.

As explained previously, the flexible tubular component is under actuated; its motion relies on the interaction with surrounding environment. Therefore, its kinematics is not fully analytical or predictable like a regular robotic arm. This issue could be solved in an iterative way by measuring errors between the predicted motion from the kinematics model at the previous step and the actual motion at the current step, and then updating the kinematics modelling accordingly. Various algorithms could be used for this part, for example, using the errors to guide updating weights for Jacobian columns, larger errors lead to greater changes to the corresponding Jacobian columns. This way of updating kinematics is helpful to improve the control accuracy and more importantly; ensure the safety of the endoscope movement by avoiding potential damage to airway walls or other tissues.

Under normal circumstances, physicians can accurately route the tubular component 2 to target points according to the navigation information. In order to better manipulate the tubular component 2, the present navigation method may further comprise the step of acquiring a visual field in front of the head 2*a* of the tubular component 2. Correspondingly, the tubular component feeding device may further comprise a visual field acquisition device 53*c* configured to acquire a visual field in front of the head of the tubular component 2.

Specifically, referring to FIGS. 3 to 6, the tubular component 2 enters a target channel 1*b* in line with the navigation path 3, and passes the first position 3*a*, the second position 3*b*, and the third position 3*c* successively. Among them, the first visual field 4*a* can be obtained when the tubular component 2 passes the first position 3*a* (see FIG. 4); the second visual field 4*b* can be obtained, when the tubular component 2 passes the second position 3*b* (see FIG. 5); and the third visual field 4*c* can be obtained, when the tubular component 2 passes the third position 3*c* (see FIG. 6).

Human tissues are movable. With contraction and expansion of lung during breath, and the involuntary movement of human tissues/organs caused by foreign sensation of an instrument, the position of the tubular component 2 in the channel may slightly shift as well. Therefore, referring to FIGS. 4 and 5, the images taken by the visual field acquisition device 53*c* on the head 2*a* of the tubular component 2 at the first position 3*a* and the second position 3*b* show a bifurcated channel at the upper left part of the target channel 1*b*. Referring to FIG. 6, the image taken by the head 2*a* of the tubular component 2 at the third position 3*c* shows a bifurcated channel at the lower right part of the target channel 1*b*.

To further improve navigation accuracy of the tubular component 2, the present navigation method may further include, after acquiring the visual field in front of the head 2*a* of the tubular component 2, the steps of: identifying channels in the visual field; selecting a target channel 1*b* from the identified channels, and correcting the current orientation of the head 2*a* of the current tubular component 2 to be toward the center of the target channel 1*b*.

Correspondingly, in the present tubular component feeding device, the correcting device 53*b* may be configured to select a target channel from the identified channels, and to correct the current head orientation of the tubular component 2 to be toward the center of the target channel.

After the visual field acquisition device 53*c* has acquired the visual field in front of the head 2*a* of the tubular component 2, the localizing device 53*a* can obtain structural features in the image by analyzing the visual field image, so as to identify bifurcation in the airway navigation to improve navigation accuracy. The correcting device 53*b* continuously corrects the orientation toward the center through image identification to correct the motion process, which can prevent the tubular component 2 from coming into contact with the inner walls of the patient's internal cavities, thereby ensuring the safety and reliability of operation.

Optionally, in the step of identifying channels in the visual field, if the identified channel possesses a bifurcation, then the branch channel planned by the navigation path 3 will be deemed as the target channel 1*b* so as to achieve automatic navigation, reduce the difficulty of physicians' operation, and improve safety.

Also, in the step of identifying channels in the visual field, if the identified channel does not possess a bifurcation, then current channel will be taken as the target channel 1*b*. In order to be always kept at the center of the pipe during motion, the tubular component 2 constantly makes self-correction to reduce or even eliminate the interference caused by human movement, so as to ensure the motion accuracy of the tubular component 2, and to improve the safety and reliability of physicians' operation. Since the center of the visual field of the camera and the center of the head of the tubular component may not be at the same position, an offset value can be preset according to the distance between the two. By making the distance between the center of the target channel and the center of the visual field to be within the preset offset value range, the head of the tubular component and the center of the target channel can always be consistent with each other, so as to better ensure the movement of the tubular component.

Referring to FIGS. 3 to 6, the tubular component 2 enters the target channel 1*b* according to the navigation path 3, and then passes the first position 3*a*, the second position 3*b*, and the third position 3*c* successively. In the example shown in FIG. 4, the tubular component 2 passes the first position 3*a*, and the first visual field 4*a* is obtained.

Figure 5:
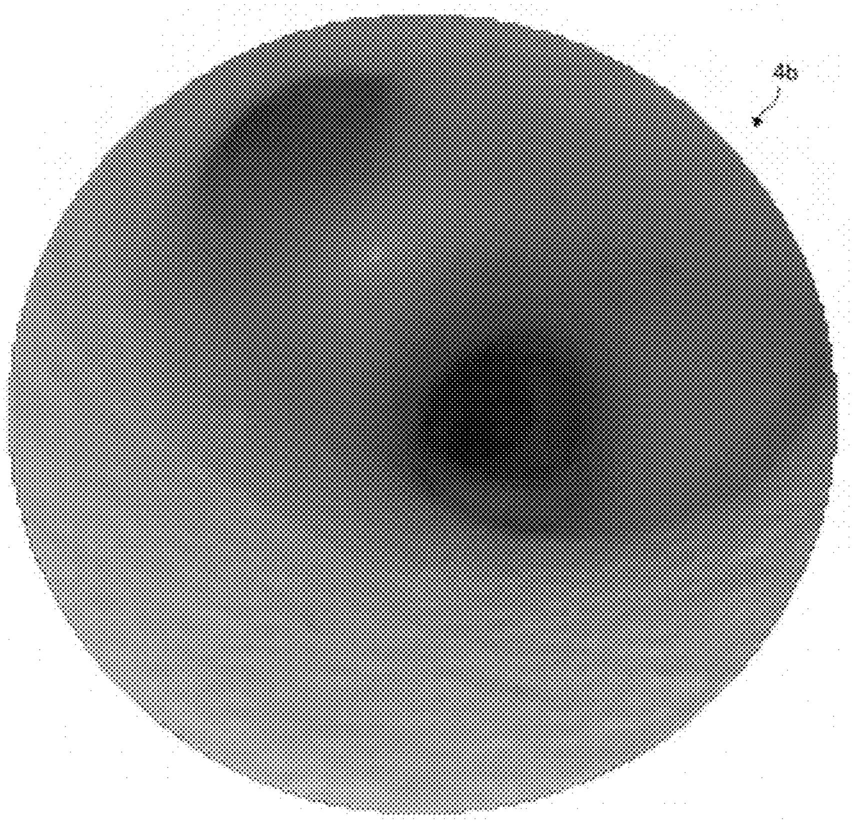
FIG. 5 is a schematic view of a shot photograph of the head of the tubular component in a second visual field at a second position.
Figure 6:
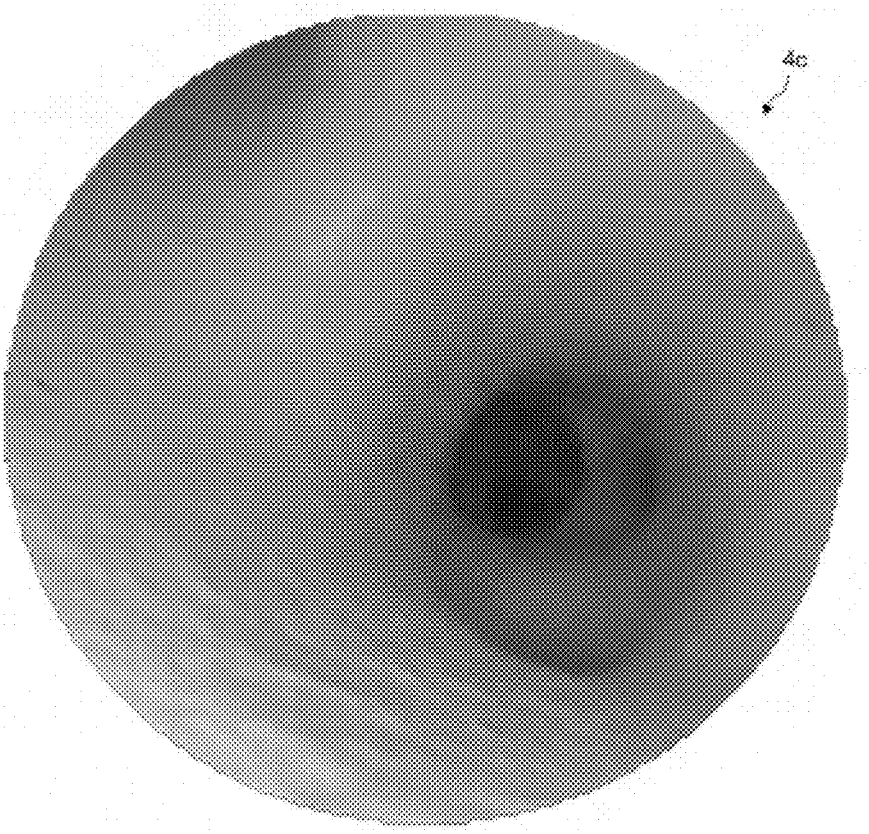
FIG. 6 is a schematic view of a shot photograph of the head of the tubular component in a third visual field at a third position.

Referring to FIG. 5, when the tubular component 2 moves on to pass the second position 3*b*, the second visual field 4*b* is obtained. There is shown a bifurcation in the channel identified by the localizing device 53*a*. The branch channel planned by the navigation path 3 is the one on the right side of the bifurcation. This branch channel planned by the navigation path 3 is now taken by the correcting device 53*b* as the target channel 1*b*. Under correction by the correcting device 53*b*, the tubular component 2 begins to turn toward the branch channel.

Referring to FIG. 6, when the tubular component 2 moves on to pass the third position 3*c*, the third visual field 4*c* is obtained. As described below, this branch channel will be localized at the center of the visual field as the tubular component 2 moves on further, such that the tubular component 2 can smoothly enter the branch channel.

Figure 7:
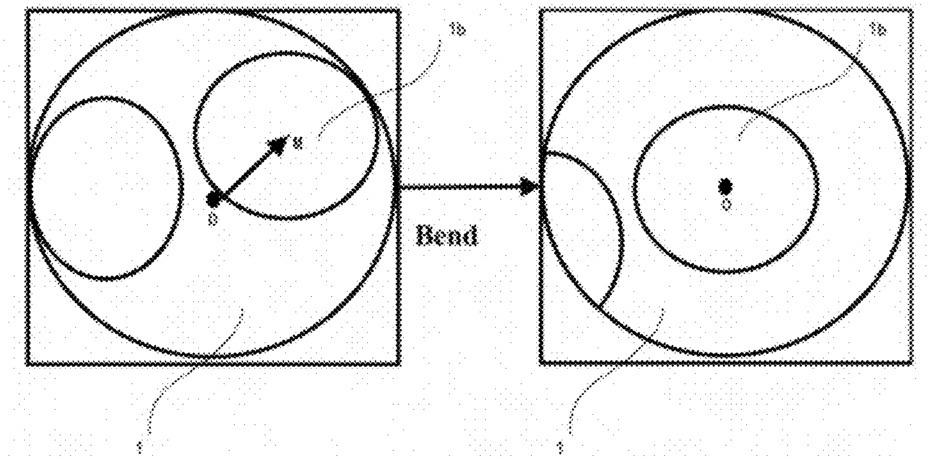
FIG. 7 is a schematic cross-sectional view of the tubular component when the orientation of its head is corrected in a direct bending way.

Additionally, referring to FIG. 7, the step of correcting the current head orientation of the tubular component 2 to be toward the center of the target channel 1*b* in the present application may further include: driving the head 2*a* of the tubular component 2 to bend toward the center of the target channel 1*b*, until the distance between the center of the target channel 16*b* and the center of the visual field is within the preset offset value range. In an embodiment, the center of the target channel 1*b* and the center of the visual field may coincide with each other. Driving the head 2*a* of the tubular component 2 to bend toward the center of the target channel 1*b* enables the tubular component 2 to achieve 360° omnidirectional movement.

More specifically, as shown in FIG. 7, point M is the center point of the target channel 1*b*. Point O indicates the center of the head of the tubular component 2, which is calibrated according to the camera parameters and the relative position between the camera and the tubular component head. Specially if the optical axis of the camera is parallel to the centerline of the head of the tubular component, point O is simply the projection of the tubular centerline onto the image plane of the camera, and there could be an offset between point O and the center of the visual field or overlapping with the center of the visual field if the camera is located at the center of the head of the tubular component. By driving the head 2*a* of the tubular component 2, the head 2*a* of the tubular component 2 will bend towards the center of the target channel 1*b*. When the points M and O are close to overlapping in the visual field, the center of the target channel 1*b* will be located at the center of the head of tubular component.

When the physicians desire to inspect a certain area of the non-target channel 1*b*, the head 2*a* of the tubular component 2 may be controlled to face the center of this area, so as to obtain a better visual field. For instance, the controller could try to make the endoscope tip perpendicular to tissue surface for better view. In this case, a computer may be used to dynamically compensate anatomy-induced motion to keep the imaging stable. Where the collected two-dimensional image is blurred, the robotic system may stop and await recovery, to ensure the safety of operation.

Endoscope in the prior art usually employs drive cable(s) to control the direction of motion of the tubular component. To achieve the omnidirectional movement, at least three or more drive cables, typically four drive cables, are required. Additionally, it is also possible to use only two drive cables to control the motion of the tubular component 2 in one degree of freedom. In this case, referring to FIG. 8, correcting the current head orientation of the tubular component 2 to be toward the center of the target channel 1*b* may further comprise the steps of: rotating the head 2*a* of the tubular component 2 so that the center of the target channel 1*b* is in a direction of freedom of the head 2*a* of the tubular component 2 in the visual field; and driving the head 2*a* of the tubular component 2 to move in the direction of freedom, so that the distance between the center of the target channel 16*b* and the center of the visual field is within the preset offset value range. In an embodiment, the center of the target channel 1*b* and the center of the visual field may coincide with each other. Here, the "direction of freedom" refers to a direction in which the head 2*a* of the tubular component 2 can freely advance and retreat.

Figure 8:
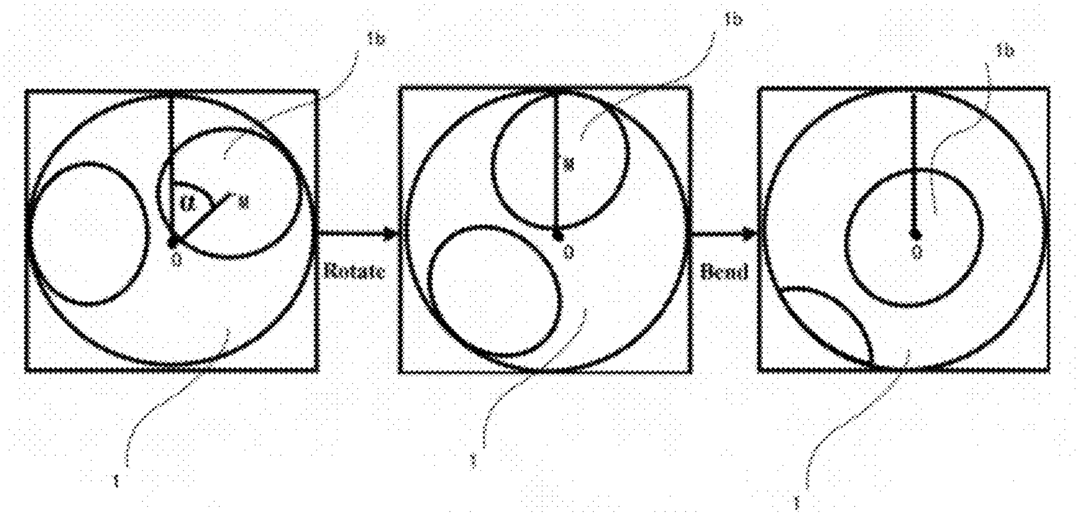
FIG. 8 is a schematic cross-sectional view of the tubular component when the orientation of its head is corrected in a way of rotating first and then bending.
Figure 9:
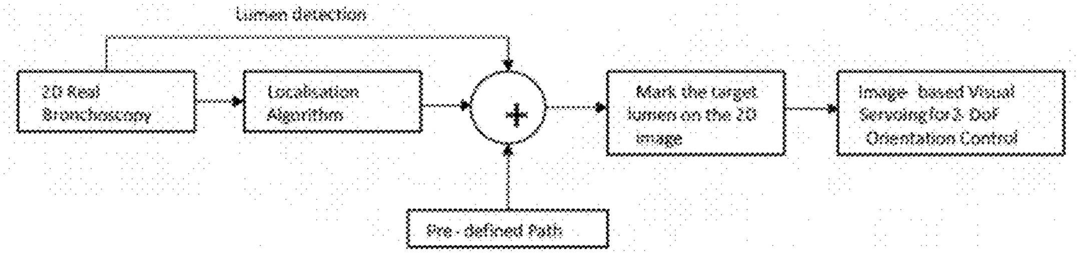
FIG. 9 is a flowchart of a method for controlling the localization and orientation of the tubular component.

In actual operation, referring to FIG. 8, point O is the center point of the head of the tubular component onto the current visual field, point M is the center point of a target channel 1*b*, and the angle between the vertical line passing through point O and the line O-M is α. By driving the head 2*a* of the tubular component 2 to rotate α° to the right or rotate (180-α)° to the left, the center of the target channel 1*b* will be in the direction of freedom of the head 2*a* of the tubular component 2 in the visual field. That is to say, point M is close to the vertical line. Finally, the head 2*a* of the tubular component 2 is driven to move in the direction of freedom. It is to be understood that when the head 2*a* of the tubular component 2 rotates to the right, the head 2*a* of the tubular component 2 will be driven to move upward accordingly; when the head 2*a* of the tubular component 2 rotates to the left, the head 2*a* of the tubular component 2 will be driven to move downward accordingly. In either case, the center of the target channel 1*b* can be localized to face the center of the head of the tubular component. That is, the point M and the point O are close to overlapping in the visual field.

The included angle α is preferably an acute angle or a right angle, to reduce the amplitude of rotation and improve the efficiency of operation. More preferably, an angle range may be set. When the included angle α is within the preset angle range, it is considered that the center of the target channel 1*b* is located in the direction of freedom of the head 2*a* of the tubular component 2 in the visual field, and the head 2*a* of the tubular component 2 can be directly driven to move in said direction of freedom, so that the center of the target channel 1*b* will be located at the center of the visual field, thereby improving the efficiency of operation.

Similarly, positions of the points O and M do not have to be completely coincident in the two-dimensional visual image, and an error range may be reserved to reduce the difficulty and to improve the efficiency of operation.

In the present application, the correcting device 53*b* is configured to drive the head 2*a* of the tubular component 2 to bend toward the center of the target channel 1*b*, until the distance between the center of the target channel 16*b* and the center of the visual field is within the preset offset value range. The correcting device 53*b* is also configured to rotate the tubular component 2, so that the center of the target channel 1*b* is located in the direction of freedom of the head 2*a* of the tubular component 2 in the visual field, and then drive the head 2*a* of the tubular component 2 to move in the direction of freedom, so that the distance between the center of the target channel 16*b* and the center of the visual field is within the preset offset value range.

Through the three-dimensional model 1*a* and the localization algorithm, the computer can determine position of the target channel 1*b* and generate the navigation information for accurate navigation. The motion process of the tubular component 2 is continuously corrected according to the established kinematic model and the way of image identification, and the correction results can further optimize the navigation information. Thus, the whole process forms a dynamic closed loop, which improves the safety and accuracy of operation.

Lumen detection is on 2D bronchoscopy images. To mark the correct target lumen, the detection algorithms needs to consider the pre-defined 3D path and current 3D location, which is obtained from the localization module, and then compare the rendered images with the real bronchoscopy images. The resulting locations of target lumen on the 2D images will be used for visual servoing or other purposes. This is explained in FIG. 9.

In practical applications, the lumen detection algorithm and the localization algorithm for the tubular component 2 can be combined to perform a real-time correction of the multi-directional navigation path 3. The lumen detection algorithm can be implemented in a high-frequency control loop, while the localization algorithm can be implemented in a low-frequency control loop, as the latter requires much more computing power. The physicians can mark a target channel 1*b* in the two-dimensional image, or mark a target location in the three-dimensional model. With the aid of visual images, the computer can directionally control the orientation of the tubular component 2, and to improve the accuracy of operation.

In order to better obtain the dynamic feedback during operation and to improve the safety and reliability of operation, the method for navigating a tubular component in the multifurcated channel in the present application may further comprise the steps of: acquiring resistance borne by the tubular component 2 during the feeding process; and feeding the resistance back to an operator via a tactile feedback device.

Figure 10:
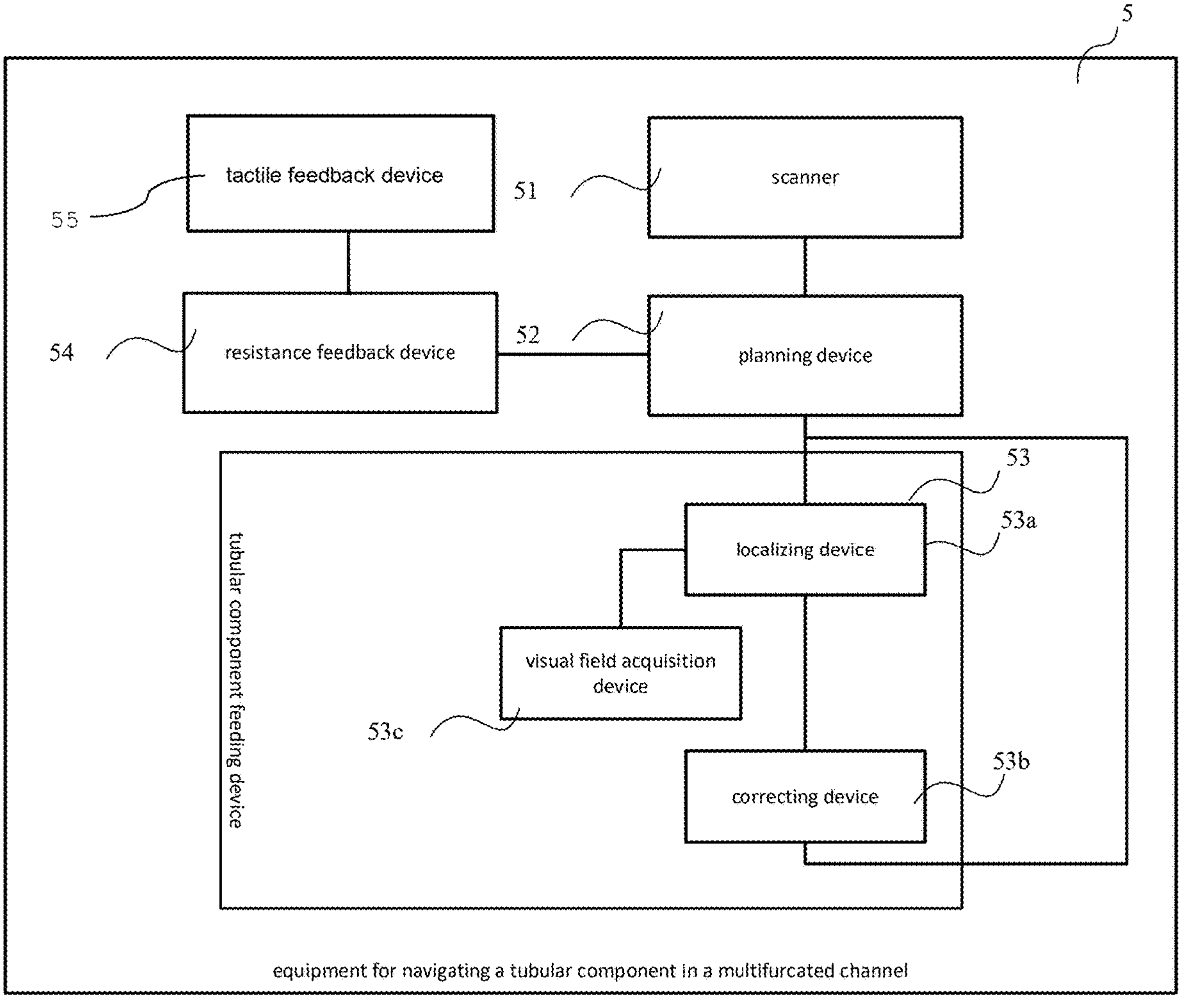
FIG. 10 is a structural block view of navigation equipment for a tubular component in the multifurcated channel.

Correspondingly, the present navigation equipment for a tubular component 2 may include a resistance feedback device 54, which is configured to acquire the resistance borne by the tubular component 2, and to feed the resistance back to an operator via the tactile feedback device 55, as shown in FIG. 10. The tactile feedback device 55 may be an electric resistance structure provided at a rocker, such as a push rod which can be driven by a motor. When the push rod acts on the rocker, further movement of the rocker can be prevented.

Specifically, the resistance feedback device 54 may be a resistance sensor provided at the head end of the tubular component 2, for measuring the magnitude of the contact force. When the tubular component 2 touches the patient's tissue, the resistance sensor will acquire and feed the resistance signal back to the tactile feedback device 55, which in turn activates the push rod to stop the rocker or even force it back into position. Of course, the resistance sensor may also feed the information back to the computer, so that physicians can adjust the operation in time to ensure the safety of operation.

The present application further proposes a computer-readable storage medium having stored a computer program. The computer program is able to perform the respective steps of the above method, when it is executed by a processor.

While the present application has been described in detail with reference to only a limited number of embodiments, it is understood that the application is not limited to such disclosed embodiments. Rather, the application can be modified to incorporate any number of variations, alterations, substitutions or equivalent arrangements which are heretofore not described, but are commensurate with the spirit and scope of the application. Further, while various embodiments of the application have been described, it is understood that each aspect of the application may include only some of the described embodiments. Generally, the application is not limited by the foregoing description, but is only limited by the scope of the appended claims.

What is claimed is:

1. A semi-automatic method for navigating a tubular component in a multifurcated channel of a patient, the method utilizing a planning device and a tubular component feeding device, the method comprising the steps of:

acquiring a three-dimensional model of the multifurcated channel of the patient;

planning, using the planning device, a navigation path for the tubular component to reach one or more target locations within the multifurcated channel according to the three-dimensional model;

using the tubular component feeding device, driving the tubular component to move within the multifurcated channel of the patient according to the navigation path, in response to the input of a forward/backward signal generated in response to a physician engaging a button or pedal, wherein the tubular component feeding device includes a visual field acquisition device to acquire a visual field in front of a head of the tubular component, a localizing device for identifying channels in an acquired visual field, and a correcting device for correcting a current orientation of the head of the tubular component;

with the tubular component moving within the multifurcated channel of the patient, acquiring a visual field inside the multifurcated channel in front of the head of the tubular component utilizing the visual field acquisition device;

identifying autonomously, by the localizing device, channels in the visual field;

selecting autonomously, by the correcting device, a target channel from the identified channels based on the navigation path; and correcting autonomously the current orientation of the head of the tubular component to be toward the center of the target channel utilizing the correcting device by:

rotating autonomously the head of the tubular component, so that the center of the target channel is located in a direction of freedom of the head of the tubular component in the visual field;

driving autonomously the head of the tubular component to move in the direction of freedom, so that the distance between the center of the target channel and center of the head of the tubular component is within a preset offset value range.

2. The method for navigating a tubular component in a multifurcated channel according to claim 1, further comprising:

determining pose information and current location information of the head of the tubular component while the tubular component moves within the multifurcated channel.

3. The method for navigating a tubular component in a multifurcated channel according to claim 1, further comprising localizing the tubular component in the multifurcated channel.

4. The method for navigating a tubular component in a multifurcated channel according to claim 1, wherein if the identified channels possess a bifurcation, then selecting autonomously a branch channel of the bifurcation planned by the navigation path as the target channel.

5. The method for navigating a tubular component in a multifurcated channel according to claim 1, wherein the multifurcated channel is a human respiratory tree.

6. The method for navigating a tubular component in a multifurcated channel according to claim 1, further comprising:

acquiring resistance borne by the tubular component while moving through the multifurcated channel of the patient;

feeding the resistance back to the physician via a tactile feedback device.

* * * * *